United States Patent [19]
Gifford, III et al.

[11] Patent Number: 4,926,858
[45] Date of Patent: May 22, 1990

[54] ATHERECTOMY DEVICE FOR SEVERE OCCLUSIONS

[75] Inventors: Hanson S. Gifford, III, Palo Alto; John B. Simpson, Woodside; Peter S. Brown, Los Altos Hills, all of Calif.

[73] Assignee: Devices for Vascular Intervention, Inc., Redwood City, Calif.

[21] Appl. No.: 391,636

[22] Filed: Aug. 7, 1989

Related U.S. Application Data

[63] Continuation of Ser. No. 45,916, May 1, 1987, abandoned, which is a continuation of Ser. No. 732,691, May 10, 1985, abandoned, which is a continuation-in-part of Ser. No. 615,298, May 30, 1984, abandoned.

[51] Int. Cl.⁵ .............................. A61F 17/32
[52] U.S. Cl. ........................ 606/159; 604/22; 606/170
[58] Field of Search ............ 128/304, 305, 305.1, 128/755, 303 R; 604/22

[56] References Cited

U.S. PATENT DOCUMENTS

| | | | |
|---|---|---|---|
| 3,614,953 | 10/1971 | Moss | 128/305 |
| 3,704,711 | 12/1972 | Park | 128/305 |
| 4,011,869 | 3/1977 | Seiler | 128/276 |
| 4,137,920 | 2/1979 | Bonnet | 128/311 |
| 4,589,412 | 5/1986 | Kensey | 128/305 |
| 4,598,710 | 7/1986 | Kleinberg et al. | 128/305 X |
| 4,601,710 | 7/1986 | Moll | 128/305 |
| 4,627,436 | 12/1986 | Leckrone | 128/303.1 |
| 4,631,052 | 12/1986 | Kensey | 128/305 |
| 4,648,402 | 3/1987 | Santos | 128/345 |
| 4,653,496 | 3/1987 | Bundy et al. | |
| 4,696,667 | 9/1987 | Masch | |
| 4,729,763 | 3/1988 | Henrie | |
| 4,732,154 | 3/1988 | Shiber | |
| 4,754,755 | 7/1988 | Husted | |

FOREIGN PATENT DOCUMENTS

| | | | |
|---|---|---|---|
| 0163502 | 12/1985 | European Pat. Off. | 128/305 |
| 67204 | 6/1969 | German Democratic Rep. | 128/305 |
| 2044103 | 10/1980 | United Kingdom | 128/305 |

Primary Examiner—Henry A. Bennet
Attorney, Agent, or Firm—Townsend & Townsend

[57] ABSTRACT

An atherectomy catheter for removal of plaque buildup from the walls of a blood vessel. The atherectomy catheter includes a cutter assembly disposed at the distal end of a flexible guide tube that may be inserted into a vessel and directed to the occlusion. A proximal actuator assembly is adapted to impart both rotary and axial movement to the cutter. The cutter assembly includes a cutter having a forwardly extending annular cutting surface. A guide wire with a flexible spring tip extends forward of the cutter for guiding the cutter as it travels axially through the artery. All of the removed atheroma materials are collected within the device and a retention member carried by the guide wire and positioned in front of the cutter forms a cap to retain the collected atheroma materials. In a disclosed embodiment, the retention member is expandable, and in one of the preferred embodiments, the retention member may be expanded to engage the vessel walls to anchor the device during the cutting stroke.

52 Claims, 9 Drawing Sheets

ATHERECTOMY DEVICE FOR SEVERE OCCLUSIONS

This is a continuation of application Ser. No. 07/045,916, filed May 1, 1987, now abandoned, which in turn is a continuation in part of co-pending application Ser. No. 732,691 filed May 10, 1985 which in turn was a continuation-in-part of application Ser. No. 615,298 filed on May 30, 1984, now abandoned. Both parent applications are incorporated herein by reference.

The present invention relates generally to atherectomy devices. More specifically, the present invention discloses an improved atherectomy device that uses a distal cutter to remove plaque buildup from the walls of a severely occluded blood or lymphatic vessel.

Coronary and peripheral vascular arteriosclerosis, known also as atherosclerosis, is a common ailment occurring in humans which involves the deposition of a fatty-like substance called atheromas or plaque on the walls of blood vessels. These plaque deposits are most common in the peripheral blood vessels that feed the limbs of the human body and the coronary arteries which feed the heart. Occasionally these fatty deposits occur in fairly localized regions of a blood vessel, thereby restricting the bloods flow and posing a serious risk to the persons health.

In the past, several methods have been attemped to restore normal blood flow through the affected vessels. Traditionally, major surgery was the only practical means of removing atheromas. More recently, there has been substantial success in increasing the size of the flow passages within plaque filled arteries through the use of a dilation process known as balloon angioplasty. However, in a substantial percentage of the cases where balloon angioplasty is used, the displaced atheroma will reoccur.

A co-pending parent application Ser. No. 732,691, discloses an atherectomy device and method for removing at least a part of an atheroma through the use of a cutting device that is inserted into the artery where the atheroma is located. A cutting edge exposed through a cutout in the side of a substantially cylindrical housing is then activated to sever a portion of the atheroma from the walls of the blood vessel. However, in the embodiments described, it is not particularly well suited for removing atheromas that substantially or totally occlude an artery.

Therefore, it is a primary objective of the present invention to provide an atherectomy device particularly well suited for removal of atheroma materials that substantially or totally occlude a blood vessel.

Another object of the present invention is to provide an atherectomy device that is both safe and efficacious.

Another object of the invention is to provide an atherectomy device capable of retaining most of the removed atheroma materials.

Another object of the invention is to provide an atherectomy device capable of removing atheromas from a wide variety of vessels, including the coronary arteries.

Another objective of the invention is to provide an atherectomy device adapted for use with a guiding wire to position the device.

A separate object of the present invention is to provide an atherectomy device having a mechanism for anchoring the cutter portion of an atherectomy device within the vicinity of the atheroma being cut.

To achieve the foregoing and other objects and in accordance with the purpose of the present invention, an atherectomy catheter for removal of material of an atheroma from a vessel is provided having a cutting assembly which can be introduced through a flexible guiding catheter. The atherectomy catheter includes a flexible drive means disposed within an outer flexible tubular member and mounted for rotary motion therein. A proximal actuator means in communication with the proximal end of the flexible drive means is adapted to provide axial and rotational movement to the cutter assembly through the drive means. The cutting assembly includes a cutter having a forwardly extending annular cutting surface and a collection chamber for retaining the removed atheroma materials. It is preferred that the drive means be tubular having an interior passage through which a flexible guide wire is passed. The guide wire is adapted for axial movement within the tubular drive means and extends forward beyond the distal extremity of the cutting assembly. Preferably, the guide wire carries an expandable member near its distal tip. Additionally, it is preferred that a flexible spring coil be provided at its distal tip to allow safer and easier advancement through the arteries.

A housing carried by the distal extremity of the outer tubular member is formed to receive the cutter to facilitate insertion of the device into a vessel. Preferably the housing is an extension of the tubular member itself.

In one of the preferred embodiments of the present invention, the expandable member is expanded to engage either the vessel walls or the atheroma itself before any cutting occurs. Thus, the expandable member serves to restrict slippage of the cutter and contain the removed atheroma material. The cutter is then advanced towards the expandable member while the cutter rotates until they abut, thereby trapping the removed portions of the atheroma within the atherectomy device.

In an alternative preferred embodiment, the expandable member is expanded as the cutting stroke is made, and serves to limit the cutter's travel as well as help retain the removed portions of atheroma within the atherectomy device.

Another preferred embodiment of the invention has a housing that covers a portion of the distal end of the cutter for reducing size of the exposed cutting edge. In this embodiment the atherectomy device includes a means for simultaneously advancing the tubular member and the drive means.

Another preferred embodiment of the invention includes a rigid member carried by the distal portion of the guide wire in place of the expandable member. The rigid member has a slightly smaller diameter than the cutter itself and passes through the occluded vessel before the cutter, thereby centering the cutter to reduce the risks of cutting into healthy portions of the artery walls. A means is provided for drawing the member into contact with the cutter for retaining the removed portions of the atheroma within the atherectomy device.

In one preferred method aspect of the invention, the guide wire is inserted into the enclosed artery so that its tip extends distally to the portion of the atheroma to be removed. The cutter is either simultaneously or subsequently introduced into the occluded artery to a position just proximal to the atheroma materials to be removed. The cutter is then advanced through the atheroma while being rotated thereby removing a portion of the atheroma. The removed atheroma materials are collected, and the device withdrawn.

The features of the present invention that are believed to be novel are set forth with particularity in the appended claims. The invention, together with further objects and advantages thereof, may best be understood by reference to the following description taken in conjunction with the accompanying drawings in which:

As illustrated in the drawings, the severe occlusion atherectomy device or catheter 1, of the present invention generically includes a cutting assembly 2, a proximal actuating assembly 3, and a flexible guiding means 7 that connects the two. The flexible guide means 7 includes a guide wire 8 disposed within a hollow center of drive tube 10. The drive tube 10 itself is received by flexible tubular member 12.

Referring first to FIGS. 1-5, one of the preferred embodiments of the cutting assembly aspect of the present invention will be described. The cutting assembly 2 is carried by the distal extremity of drive tube 10 and includes a cutter 4 having an annular cutting edge 5. A housing 6 which in this embodiment is an enlarged extension of tubular member 12 fully receives cutter 4 such that cutting edge 5 is not exposed.

The cutter 4 is substantially cup shaped and has an interior collection chamber 14. As can best be understood with reference to FIG. 4, as a portion of the atheroma 99 is severed from the walls of artery 98, the forward motion of the cutter directs the removed atheroma materials into collection chamber 14. It is important to retain the atheroma materials removed to prevent the loose pieces from flowing downstream through the arteries and causing blockage elsewhere. A side benefit of retaining such material intact is that the large chunks also provide excellent biopsy samples.

Figure 2:
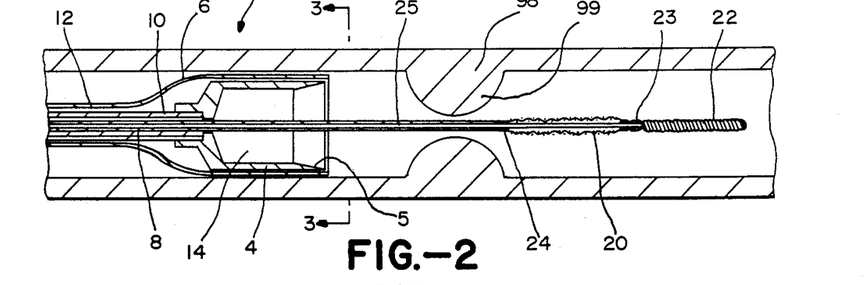
FIG. 2 is a cut-away side elevational view of the cutting assembly shown in FIG. 1.
Figure 3:
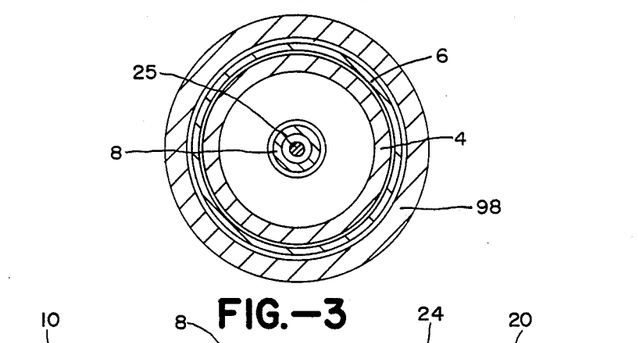
FIG. 3 is a cross-sectional view of the cutter assembly shown in FIG. 2 taken along lines 3—3.

The cutter 4 is adapted to recess within housing 6 when the atherectomy device 1 is not in use. Thus, cutting edge 5 is not exposed to the fragile vessel walls while cutting assembly 2 is being fed through the blood vessel in route to or from an atheroma. This significantly reduces the risks of traumatizing the cleaned vessel that would otherwise be associated with the atherectomy device's use.

Cutter 4 may be fashioned from any suitable material or combination of materials, so long as its leading edge may be formed into an effective cutting edge 5 and the material does not have any adverse health implication when placed within a bloodstream. There are a large number of metals, plastics and ceramics which could be used. An example of a suitable cutter material is a thin stainless steel ring that is ground on its leading edge to form annular cutting surface 5.

Flexible guide wire 8 carries a retention means 20 near its distal end. In this embodiment retention means 20 takes the form of an expandable member 20 that may be separately actuated and has multiple functions. First, it may be enlarged to engage the artery walls or the atheroma itself to limit slippage of the cutter. Second, it limits the cutter's translation through an artery. Third, it works essentially as a cap for collection chamber 14 to hold the removed atheroma materials.

The distal extremity of guide wire 8 has a spring tip 22 that increases its resilience and allows the guide wire to readily pass through tortuous vessels without causing damage to the vessel walls. It is contemplated that spring tip 22 may be attached to guide wire 8 by any conventional method. By way of example, one appropriate method would be to place a tightly fitting sprig about the tip of guide wire 8 and solder the two pieces together.

Testing has shown that in order to advance a cutter through heavy deposits of plaque, it must be pushed somewhat. Since each of the cutters of the present invention are located at the distal end of an extended drive tube, it is often difficult to apply this pushing force. Therefore, we have developed several mechanisms for preventing such slippage. Generically, a device having a distal tip much smaller than the cutter and carrying an expandable member near its distal end, is pushed across the lesion. The expandable member is advanced into the middle of, or across a lesion and is subsequently opened in the radial direction far enough to engage the either the artery walls or the atheroma itself, the expandable member will in effect anchor the device and resist being pulled back. Thus, the expandable member may be used as an anchor urging any relative movement between cutter and itself to be primarily in the form of the cutter moving forward.

Figure 4:
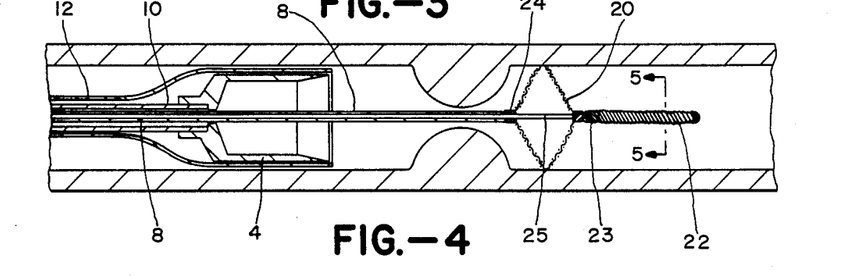
FIG. 4 is a cut-away side elevational view of the cutting assembly shown in FIG. 2 with its basket expanded.
Figure 5:
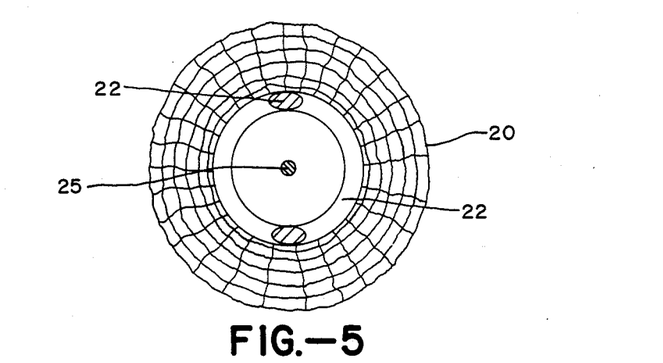
FIG. 5 is a cross-sectional view of the cutter assembly shown in FIG. 4 taken along line 5—5.

In the embodiment shown in FIGS. 2 and 4, the retention means takes the form of an expandable member that is capable of providing such an anchoring force. This is, expandable basket 20. The expandable basket 20 is fashioned in a meshed arrangement from a plurality of braided wires that are attached together on opposite ends. Basket 20 and its braids 29 are sized such that when compressed axially, it will have a radial width slightly larger than cutting surface 5 of cutter 4. The compressed diameter of the braid is preferably approximately a half of a millimeter. Its expanded radial diameter is preferably in the range of approximately 2-3 millimeters.

To facilitate radial expansion and compression of the basket 20, guide wire 8 is a hypodermic tube having an extremely small co-axial lumen 21 running therethrough. The lumen diameter may be in the range of 0.005 to 0.010 inches. An expansion wire 25 is threaded through the hypo tube 8 and forms the core of the spring tip 22. The proximal end 24 of basket 20 is attached to the hypo tube 8, while the distal end 23 of basket 20 is attached to the expansion wire 25. These attachments may be made using any conventional technique. By way of example, they may be attached by soldering or brazing.

To expand the basket 20, an expansion means 76 is provided on the proximal end of guide wire 8. The expansion means 76 pulls backwards on wire 25 relative to hypo type 8. This causes basket 20 to compress axially thereby forcing radial expansion. In contrast, if wire 25 is pushed forward within hypo tube 8, the basket 20 flattens out. A simple screw-threaded mechanism with knurled outside diameters located on the proximal end of guide wire 8 is one example of an expansion means that would allow the doctor to activate the basket easily.

Braided basket 20 may be constructed from a plurality of wires, with the optimal number of wires depending upon the material used. If, for example stainless steel is the chosen braid material, an effective basket could be formed using between 10 and 50 stainless steel wires, with the most preferred range being between about 16 and 32 strands.

Figure 1:
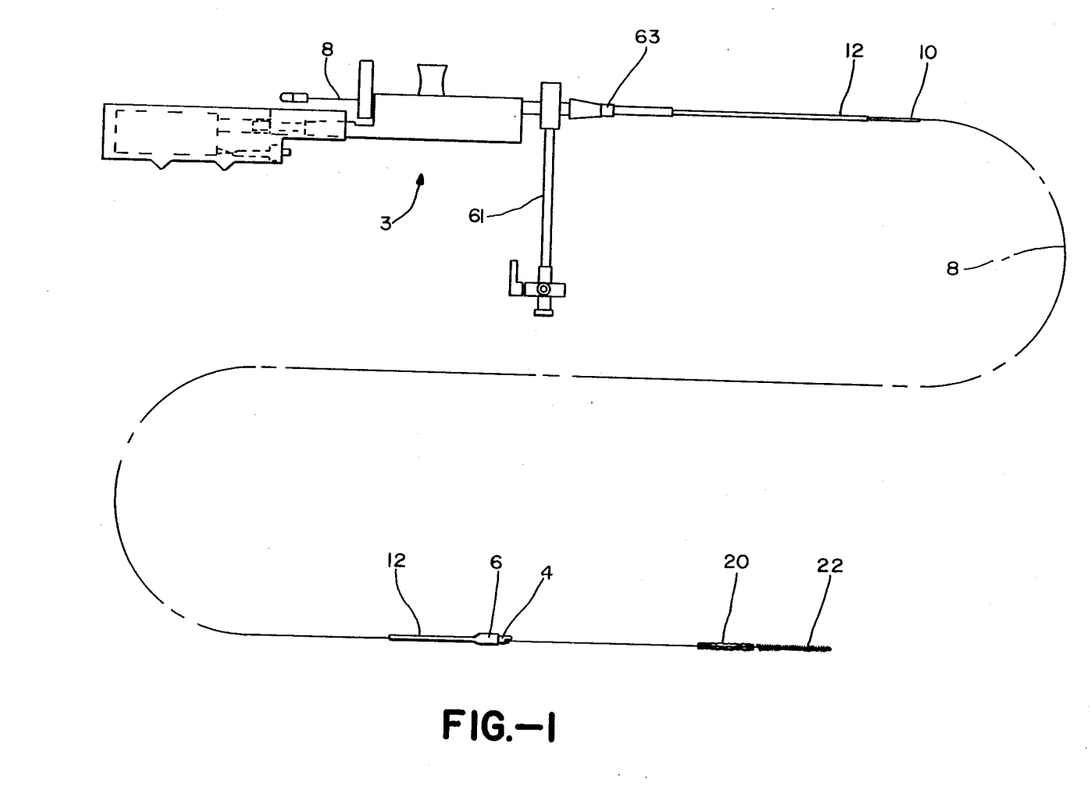
FIG. 1 is a side elevational view of an atherectomy device incorporating the present invention.
Figures 6, 7:
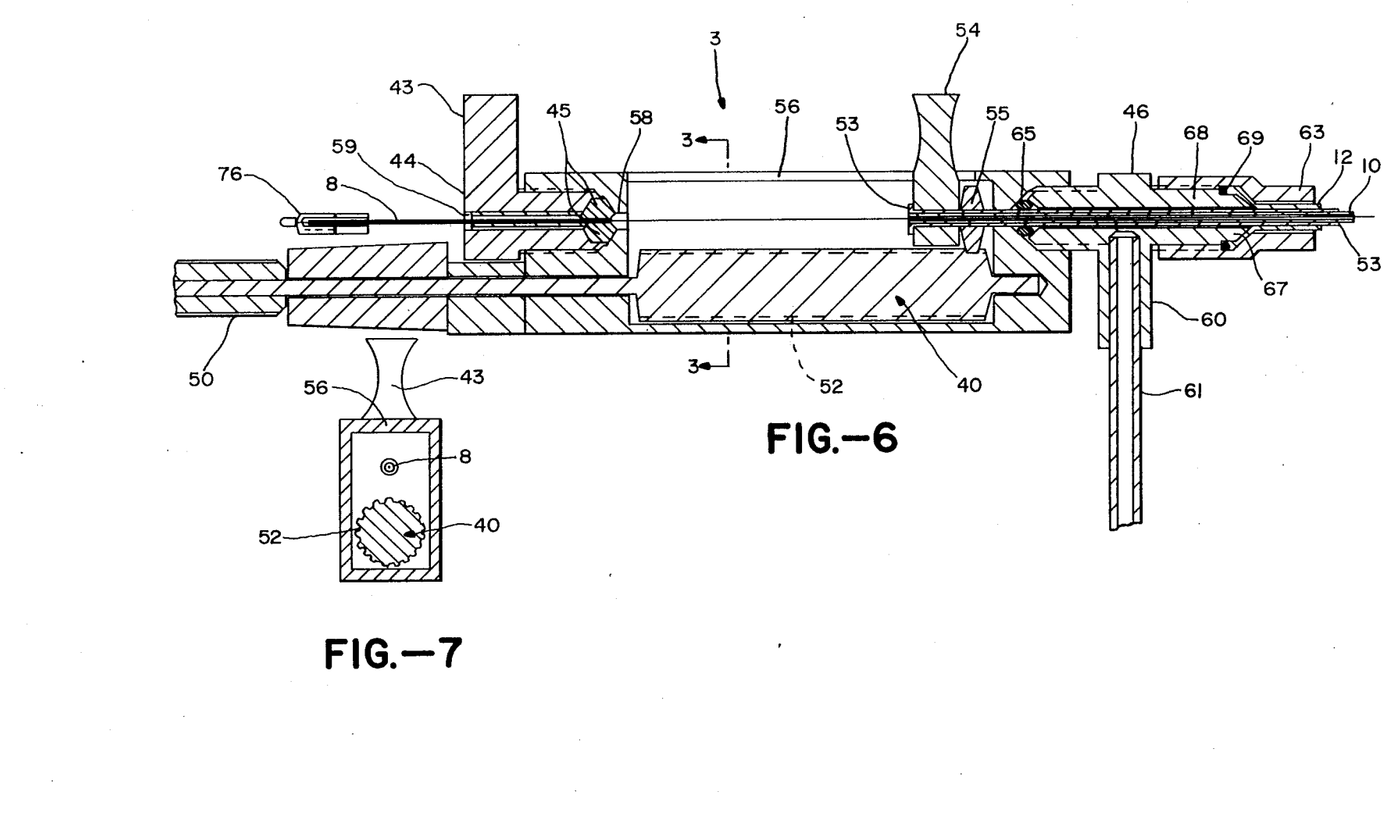
FIG. 6 is a cut-away side elevational view of the proximal actuator assembly shown in FIG. 1.
FIG. 7 is a cross-sectional view of the proximal actuator assembly shown in FIG. 6 taken along line 7—7.

The operation of the braided atherectomy device can best be understood by referring to FIGS. 1 and 2. Guide wire 8 is first inserted into an occluded vessel 98 and advanced until braided basket 20 extends just beyond the atheroma 99 to be removed. The remainder of the atherectomy device is then introduced over the guide wire 8 and advanced until the distal end of cutter 4 essentially abuts against atheroma 99. A guide wire locking means 43 (as seen in FIGS. 1 and 6) located on the proximal actuator assembly 3 is then activated to securely fix the guide wire 8 relative to tubular member 12 and thus housing 6. A rotating means disposed on the actuator assembly causes drive tube 10 to rotate within tubular member 12 which remains substantially fixed in position. A translation means 54, also disposed on the actuator assembly allows selective control of the translation of cutter 4 as it egresses from housing 6 while rotating. The spinning cutter is slowly advanced, thereby cutting a path through the blockage. Preferably, the cutter 4 would be spun at a rate in the range of between 1500 to 2500 revolutions per minute.

A proximal actuator assembly 3 adapted for use with the cutter assembly just described is shown in FIG. 6. Actuator assembly 3 includes housing 37, cutter control means 40, a guide wire locking means 43 and a cutter locking means 46. The housing 37 is fixably secured to the proximal extremity of tubular member 12.

The cutter control means 40 is disposed primarily within housing 37 and couples to the proximal extremity of flexible drive tube 10. Cutter control means 40 is adapted to independently impart both rotary and axial movement unto the drive means 10. The embodiment shown includes an offset extended cylindrical gear 52 at the distal end of a drive shaft 50. The drive shaft is offset to accommodate attachment to a motorized drive unit (not shown) capable of rotating the shaft at a high angular velocity. An example of a suitable motorized drive unit is disclosed in co-pending application Ser. No. 834,743, filed Feb. 28, 1986. It should be appreciated, however, that an in-line drive shaft could just as readily be used. Particularly when combined with a hand operated knob or a motorized drive unit having a hollow drive shaft for imparting rotary motion to the drive tube.

Cylindrical gear 52 engages a drive gear 55 directly connected to a plunger 53 which forms an extension of drive tube 10. Thus, any rotation in drive shaft 50 causes a corresponding rotation in drive tube 10. The gearing ration between cylindrical gear 52 and drive gear 55 may be varied to suit a particular purpose. Arm 54 which is also connected to plunger 53, extends through a slot 56 in housing 37 thereby allowing the doctor to translate drive tube 10 axially relative to housing 37 and thus relative to fixed tubular member 12. Since cutter 4 (see FIG. 2) is recessed within an extension of tubular member 12, arm 54 directly controls the ingressing and egressing of cutter 4 relative to its housing 6. Arm 54 is moved manually by the doctor, preferably using thumb pressure. Although the translation of drive tube 10 is controlled by a manual mechanism in this embodiment, it is contemplated that the translation of cutter 4 could be mechanized. For example, it could be geared to the rotational movements.

Plunger 53 is a hollow cylinder having a borehole that aligns with both the lumen within drive tube 10 and an aperture 58 in housing 37. Thus, guide wire 8 may freely pass therethrough. However, basket expansion means 76 located on the proximal end of guide wire 8 is too large to enter aperture 58. Guide wire locking means 43 is formed by a friction lever 44 disposed on the exterior of housing 37 adjacent to aperture 58. The friction lever 44 is threadably attached to housing 37 co-axially with aperture 58. A pair of wedge shaped clamps 45 are placed between friction lever 44 and the housing adjacent to aperture 58 so that rotation of friction lever 44 will cause wedges 45 to clamp down on guide wire 8 thereby locking it in place.

After the cutter assembly has been properly positioned over guide wire 8 so that cutter 4 is in place next to the atheroma to be removed, friction lever 44 is activated to firmly lock guide wire 8 in relation to the housings 37 and 6. This insures that as cutter 4 advances, the guide wire 8 and the expanding member 20 that the guide wire carries will remain in place.

Cutter locking means 46 takes the form of clamp arm 60 and is disposed on the distal side of housing 37 near the proximal end of drive tube 10. Clamp arm 60 is T-shaped having two co-axial threaded arms which are also co-axial with the drive tube 10. The distal threaded arm 68 includes a reduced diameter extension 67 which is sized to receive the flared proximal end of tubular member 12. When clamp arm 60 is rotated relative to housing 37, it compresses an O-ring 65 which presses down on plunger 53. This action prohibits plunger 53 and thus, drive tube 10 from moving axially. By locking drive tube 10 in place, cutter 4 is held in place relative to guide wire 8 which is fixed in place by guide wire locking means 43. The primary purpose of clamp arm 60 is to keep cutter 4 in contact with expandable member 20 after the cut has been made. This insures that the collected atheroma materials do not get loose. During normal operation clamp arm 60 remains open, thus O-ring 65 does not press tightly against plunger 53, thereby allowing drive tube 10 to freely move under the influence of cutter control means 40. However, after the cut has been made and the expandable member 20 has been brought into contact with cutter 4, clamp arm 60 is rotated to compress O-ring 65 and clamp drive shaft 10 in place to maintain that abutting relationship between the cutter and the expandable member until the catheter has been withdrawn from the body.

In addition to pressing against plunger 53 to hold drive tube 10 in place, O-ring 65, when compressed slightly seals around plunger 53 to prevent the backflow of blood through the gap between drive tube 10 and tubular member 12, while still allowing the plunger to be advanced and retracted. Thus, before the atherectomy device is inserted into the patients body, clamp arm 60 is tightened slightly so the O-ring 65 forms a seal with plunger 53.

The distal threaded arm 68 of clamp arm 60 is threadably received by adapter 63. The proximal end of tubular member 12 is flared to receive the reduced diameter extension 67 of the distal threaded arm 68 between clamp arm 60 and adapter 63. Tightening adapter 63 on threaded arm 68 firmly secures tubular member 12 in place. A second O-ring 69 occupies the gap between adapter 63 and threaded arm 68 by the reduced diameter extension 67. The second O-ring also functions to prevent blood from backflowing between the tubular member 12 and drive tube 10.

In the embodiment shown, clamp arm 60 also acts as a fluid entry port 61. The fluid entry port 61, inter alia, facilitates a standard sterile flush of the instrument by allowing the doctor to introduce a spline solution into the atherectomy device to remove all air and gases trapped therein before the device is inserted into a body. Additionally, if it is desirable to introduce radioscopic studies, they may be introduced through the fluid entry port using conventional techniques that are well known by those skilled in the art.

To remove an atheroma, a sterile device is opened, inspected and tested. The device is then flushed with a sterile solution introduced to fluid entry port 61 through a stopcock (not shown). The device is then introduced into a vessel through a guiding catheter (not shown) using conventional techniques. Guide wire 8 is advanced far ahead of the device and across the lesion. The cutting assembly is then advanced up to the lesion. The distance from the distal end of cutter 4 to the proximal end of the basket 20 should be approximately 0.200 inches. Friction lever 44 is then tightened, locking the guide wire 8 in place. Expansion means 26 is then activated to expand basket 20, thereby holding the distal tip in place. Drive shaft 50 is then rotated and arm 54 is pushed forward thereby advancing cutter 4 across the lesion until it abuts against basket 20. Clamp arm 60 is tightened to keep cutter 4 abutting against basket 20 and the device is withdrawn. If necessary, the process can be repeated to remove extended blockages.

It will be appreciated that there are a wide variety of alternative structures that could be used to accomplish the functions carried out by the cutter control means 40, guide wire locking means 43, cutter locking means 46 and fluid entry port 61. For example, there are numerous mechanisms for imparting rotary motion to drive tube 10. Drive shaft 50 could be a direct proximal extension of drive tube 10. Alternatively an expanded hand operated knob could be provided at the end of the drive tube 10 to facilitate manual rotation of the cutter.

Figure 8:
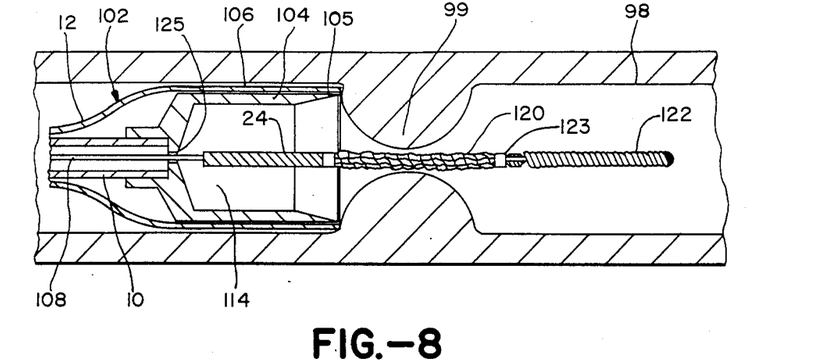
FIG. 8 is a cut-away side elevational view of an alternative embodiment of the cutter assembly of the present invention having an expandable basket that is actuated by abutting against the cutter.
Figure 9:
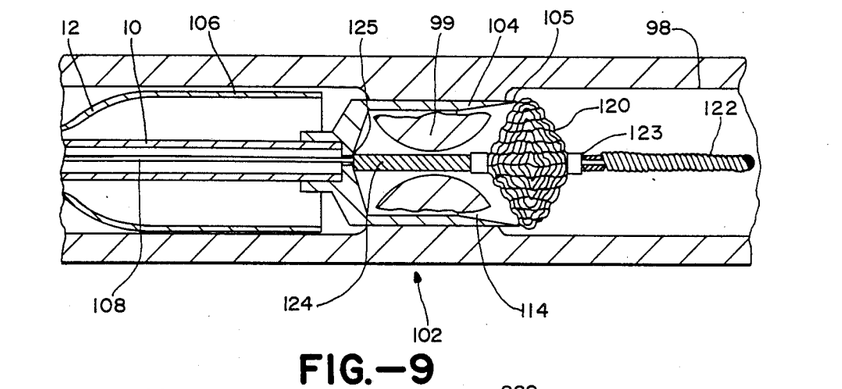
FIG. 9 is a cut-away side elevational view of the cutter assembly shown in FIG. 8 as it cuts through an atheroma.

FIGS. 8 and 9 show an alternative embodiment of the invention that is identical to the embodiment just described in all respects except for the manner in which the braided basket 20 is actuated. Instead of having a separately actuatable basket, the expandable member 20 is actuated by the stroke of the cutter itself. Thus, there is no need for the guide wire 108 to have a central lumen and the expansion means consists solely of components found near the device's distal tip.

As before, the expandable member 20 takes the form of a braided basket 120 which is fashioned from a plurality of meshed braided wires 129. However, in this embodiment, the distal end 123 of braided basket 120 is firmly secured to the guide wire 108, while an enlarged proximal end 124 loosely; fits about the guide wire 108. Thus, basket 120 may freely compress and expand in the axial direction. Compression in the axial direction causes expansion in the radial direction. Similarly axial expansion causes radial compression. It is contemplated that basket 120 will be positioned sufficiently close to the proximal bottom end 125 of collection chamber 114 to insure that when a cut is made, the enlarged proximal end 124 of basket 120 will abut against the cutter, thereby causing the proximal end of basket 120 to translate along side cutter 104. The axial stroke of the free proximal end 124 of basket 120 should be selected such that braided basket expands sufficiently in the radial direction to cover the open face of cutter 104.

As cutter 104 advances, the proximal end 123 of braided basket 120 comes into contact with drive tube 10. Since the distal end 123 of braided basket 120 is fixed in position on the guide wire, when its free proximal end 124 abuts against drive tube 10, the braided portion compresses axially, causing expansion in the radial direction. Basket 120 and its braids 125 are sized such that when fully compressed, it has a radial width substantially the same diameter as, or slightly larger than, cutting surface 105 of cutter 104. Therefore, braided basket 120 may be drawn to abut against the cutter and functions as a cap that holds the severed portion of atheroma 99 within the cutting assembly. The cutter 104 is then preferably locked into place relative to braided basket 120 via a retention locking means 46 located on actuator assembly 3. The compressed diameter of the braid is approximately a half of a millimeter, while its expanded diameter is in the range of approximately 2-3 millimeters.

It will be apparent that the braided basket in this embodiment does not function as an anchor to urge cutter 104 to egress from its housing 106 as did the expandable member in the previous embodiment. However, this embodiment is quite effective at retaining the removed portions of atheroma within collection chamber 114. Therefore, the actuator assembly 3 shown in FIG. 6 and 7 could be used to control the cutting assembly 102. The only difference in the proximal actuator assemblies would be that the latter embodiment has no use for expansion means 76 on the proximal end of the guide wire.

Figure 10:
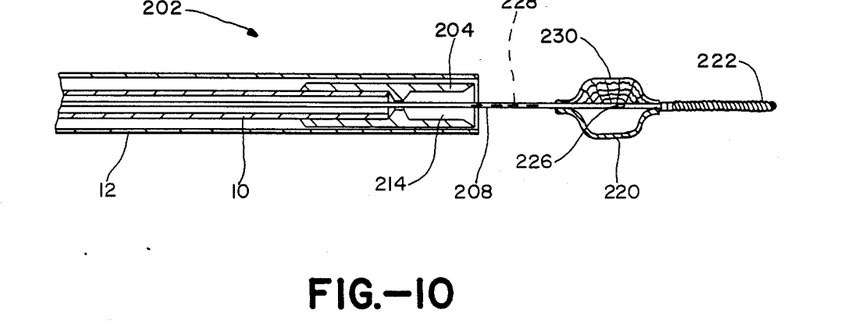
FIG. 10 is a cut-away side elevational view of yet another embodiment of the cutter assembly of the present invention that features an inflatable balloon anchoring system.

FIG. 10 presents another alternative embodiment that utilizes a high-pressure balloon to both cap the collection chamber 214 and anchor the distal end of the atherectomy catheter. In this embodiment, the guide wire is again in the form of a hypo tube 208. A high pressure balloon 220 is sealably attached near the distal end of guide tube 208 in approximately the same location that the baskets described in the previous embodiments were placed. Balloon 220 is sized large enough to engage, yet small enough not to stretch, the walls of artery 98. An aperture 226 located near the distal end of hypo tube 108 vents hypo lumen 228 within the high pressure balloon 220. Preferably the hypo tube 208 has an exterior diameter in the range of 0.010 to 0.015 inches. Balloon 220 is preferably inflated to a pressure of at least 80 psi using a saline solution. Although gases could be used to inflate the balloon, they are discouraged since if the balloon were to inadvertently burst, there would be a great danger of embolisms causing damage in other parts of the body.

The balloon anchoring system can also be adapted to function as a cap for the collection chamber within cutting assembly 202 in a manner similar to the braided basket described in the previous embodiment. Thus, cutter 204 would finish its cutting stroke lying against the balloon, thereby trapping the severed portion of the atheroma inside the cutter. The device is then removed, keeping at least a partially inflated balloon pressed against the cutter to retain the trimmed plaque.

In embodiments where the balloon 220 is expected to limit the cutting stroke and/or form a seal for cutter 204, an expandable protective sheath 230 may be placed about the balloon to prevent the cutter 204 from causing damage to the balloon 220 itself. In the embodiment shown, protective sheath 230 takes the form of a braided mesh. The mesh material may be formed of any material that is acceptable within the confines of a blood vessel and will not be easily cut when it is contacted by the spinning cutter 204. By way of example, stainless steel would be an appropriate material to form the mesh.

The rigid cutters described above work excellently for cutting relative narrow atheromas. However, since the length of collection chamber 14 is relatively short, they all have a relatively limited collection capacity. The permissible length of a rigid cutter is primarily limited by the tortuous nature of the arteries through which the cutter must pass. Therefore, rigid structures ranging from ½ to 1 inch long are well suited for cleaning relatively straight vessels. However, when smaller vessels such as coronary arteries are encountered, the rigid structure must be much smaller.

The length of the collection chamber becomes a major concern when attempting to remove extended blockages. The shorter the collection chamber is, the greater will be the number of required cleaning passes. Since each cleaning pass requires the insertion and withdrawal of the catheter, a shorter collection chamber will increase both the risk of infection and the time required for the surgery. Therefore it is desirable to have a flexible collection chamber.

Figures 11, 12, 13, 14:
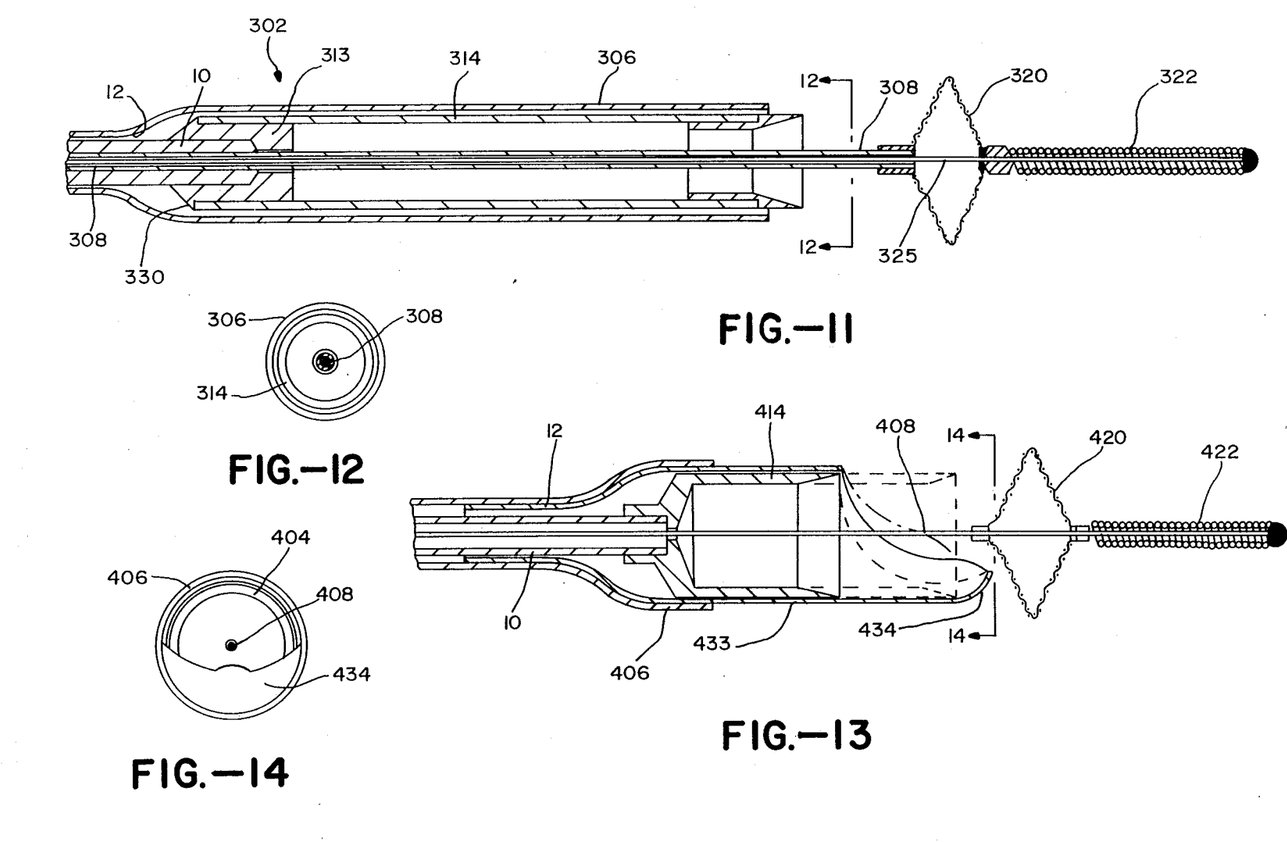
FIG. 11 is a cut-away side elevational view of another embodiment of the present invention that features an elongated, flexible collection chamber with a separately actuated basket.
FIG. 12 is a cross-sectional view of the cutter assembly shown in FIG. 11 taken along the line 12—12.
FIG. 13 is a cut-away side elevational view of yet another embodiment of the cutter assembly of the present invention that is adapted to remove atheroma materials from only one side of a vessel's wall.
FIG. 14 is a cross-sectional view of the cutter assembly shown in FIG. 13 taken along the line 14—14.

Referring now to FIGS. 11 and 12, an alternative embodiment of the cutter assembly will be described which features an elongated flexible collection tube 314. Such a design facilitates the removal of extended blockages in a single, or a reduced number of passes. Cutter assembly 302 includes an annular cutter 304, a drive tube connector 313 and an elongated flexible collection tube 314 running between the two.

As in the previously described embodiments, the cutter assembly 302 is connected to a proximal actuator assembly 3 via a flexible guiding means 7 that includes a flexible tubular member 12 through which a flexible drive tube 10 is passed. Drive tube 10 has a hollow center through which guide wire 308 may freely pass. The retaining means, which takes the form of braided basket 320 is adapted to be separately actuated in this embodiment. Therefore, guide wire 308 is a hypodermic tube having an extremely narrow lumen running co-axially with the tube.

The construction and operation of cutter assembly 302 is similar to that previously described with respect to cutter assembly 2, although it is adapted to collect much larger sections of the severed atheroma. As before, cutter 304 takes the form of an annular ring. The drive connector 313 directly engages drive tube 10 and includes an annular ridge 330. The flexible collection chamber 314 runs between cutter 304 and connector 313 and tightly receives each on its respective ends. Connector ridge 330 abuts directly against collection chamber 314. Thus, when drive tube 10 is rotated, drive connector 313, collection tube 314 and cutter 304 all rotate simultaneously.

The collection tube 314 may be fashioned from any flexible material, including those disclosed in co-pending application Ser. No. 834,947. One preferred embodiment, however, is a braided type housing. The braided construction is formed by braiding fibers in at least a single layer braid and then coating the fibers and filling the interstices between the braided fibers to increase the strength of the braided tube or tubing. Thus, by way of example, the braided tube can be formed of suitable fibers, such as of stainless steel having a thickness ranging from two mils to three mils and preferably having a thickness of approximately 2.5 mils. Thereafter, the stainless steel fibers can be coated with epoxy or a plastic such as polyurethane. This can take the form of dipping the fibers into a polyurethane bath. The polyurethane is permitted to dry and harden to provide a generally cylindrical tube which holds its shape while still being flexible. With this construction, even though cutter assembly 302 is quite flexible, it will not kink or bend as it works its way through a tortuous vessel.

One of the principal advantages of the flexible nature of this cutting assembly is that it may be used to remove extended plaque buildups within some of the smaller vessels in the human body such as the coronary arteries associated with the heart. It is particularly important to be able to clean the coronary arteries since atheromas within the coronary arteries are a major cause of heart attacks and the need for coronary bypass surgery.

A proximal actuator assembly identical to the one disclosed in FIGS. 6 and 7 could be used to control the flexible cutting assembly 302 disclosed herein. It should be understood, however, that the flexible collection chamber could be used with any of the embodiments disclosed in this application.

Yet another embodiment of the cutter assembly of the present invention, referred to as a side cutting atherectomy device will be described with reference to FIGS. 13 and 14. Most atheromas tend to grow asymmetrically about the artery walls. In many cases, one side of an artery wall will be virtually clean while the opposing wall is heavily covered with plaque. In such cases, it is undesirable to expose the relatively clean portions of the artery walls to the cutter's blade.

The construction of the side cutting atherectomy device is similar in most respects to the previously discussed embodiments. However, its housing 406 has an asymmetrical elongated sheath 433 that extends forward at least as far as the cutting edge 405 is free to travel relative to the housing. As before, the housing 406 completely encases cutter 404 when the cutter is withdrawn for insertion into a vessel. Sheath 433 is cut away asymmetrically on its distal extremity so that when the cutter 404 is advanced, one of its sides is exposed, while the other side remains within the confines of sheath 433. To facilitate a cutting stroke of reasonable length, tubular member 12 and thus, housing 406 is adapted to translate with the cutter 404 during the cutting stroke. A mechanism is also provided to egress the cutter from the fully encased portion of housing 406 prior to the cutting stroke.

As will be readily recognized by those skilled in the art, the cutter can be egressed into the sheath portion and then the housing caused to translate with the cutter via a wide variety of mounting techniques. By way of example, a suitable mounting technique for egressing the cutter would be to provide a tubular extension on the proximal actuator assembly that encases the entry of the flexible guide means. Additionally, an extension sleeve is secured to the proximal end of tubular member 12. The extension sleeve is sized so that it is slideably couples the tubular extension on the proximal actuator. An O-ring disposed about the tubular extension seals the connection between the extension sleeve and the tubular extension to prevent the backflow of blood. With this construction, the length of the tubular member 12 is sized so that when the sleeve abuts against the proximal actuator assembly, cutter 404 is positioned within the open portion of the sheath, and when the sleeve is slid forward, the cutter is recessed within the completely protected portion of housing 406. After the cutter assembly has been inserted into the artery and is properly placed adjacent to the atheroma, the doctor pulls the sleeve backwards, thereby exposing the cutter. The actuator plunger 53 (as shown in FIG. 6) is then adapted to translate drive tube 10 and tubular member 12 simultaneously.

Preferably, to further prevent the cutter from damaging the artery walls, sheath 433 is curled up at its distal extremity forming a rounded tip 434 that encases the lower portion of cutting edge 405. This reduces the possibility that the sharp cutting edge 405 will scratch or traumatize the healthy portions of the artery walls. The actual contour of the asymmetrical sheath may vary widely dependent on the size of the atheroma to be removed and its specific location. Representative contours are shown in FIG. 14.

Figure 15:
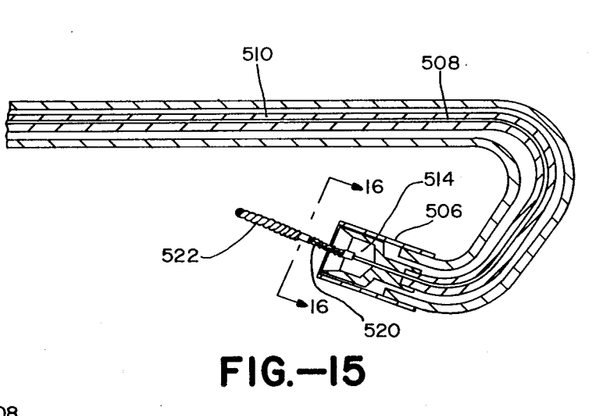
FIG. 15 is a cut-away side elevational view of another embodiment of the cutter assembly of the present invention that has an enlarged cutter.
Figure 16:
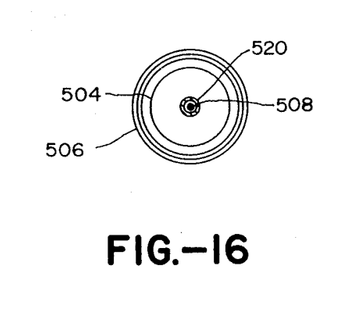
FIG. 16 is a cross-sectional view of the cutter assembly shown in FIG. 15 taken along line 16—16.

FIGS. 15 and 16 show an alternative housing arrangement adapted to contain a larger sized cutter 504 for a given size flexible tubular member. This embodiment is in all respects equivalent to the embodiment shown in FIG. 2 except that unlike the housing 6, housing 506 is not an extension of tubular member 12. Rather, when fully recessed, the proximal side of cutter 504 abuts against the distal side of tubular member 2. Thus, housing 506 is a thin walled tube that receives the distal end of tubular member 12 and the recessed cutter 504. Housing 506 may be formed from any thin-walled material that is compatible with use in the blood stream. Representative appropriate materials include various plastics and stainless steel.

To facilitate larger diameter cutters, it may be desirable to use a flexible guiding means having outer diameters in the range of 3 to 4 millimeters. In such embodiments, diameter of annular cutter 504 would also be in the range of 3 to 4 millimeters. To facilitate introduction of a cutter this size into the coronary arteries, it may be desirable to shape flexible guide means 7 in the form of a standard coronary guiding catheter such as that made by Devices for Vascular Intervention of Redwood City, Calif. This can easily be straightened for introduction by using a guide wire 508 that is stiff in its proximal section. By way of example, the last 10 to 20 centimeters of the guide wire could be flexible, thereby still allowing the cutter assembly 502 to pass through tortuous vessels while providing the required rigidity.

Figure 17:
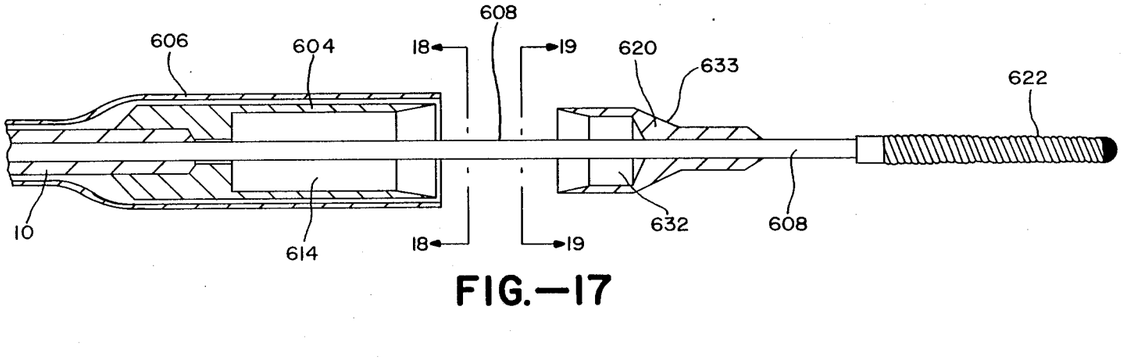
FIG. 17 is a cut-away side elevational view of another embodiment of the cutter assembly of the present invention that features a leading bullet.
Figure 18:
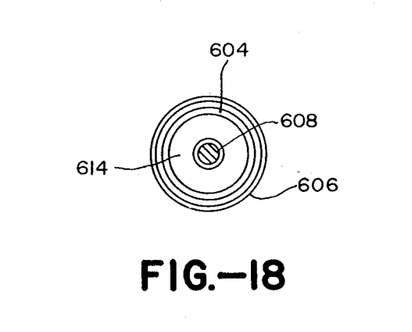
FIG. 18 is a cross-sectional view of the cutter assembly shown in FIG. 17 taken along line 18—18.
Figure 19:
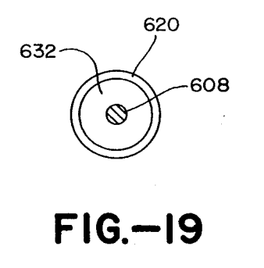
FIG. 19 is a cross-sectional view of the cutter assembly shown in FIG. 17 taken along line 19—19.

Still another embodiment of the cutter assembly for the present invention is shown in and described in FIGS. 17, 18 and 19. In this embodiment, retention means 20 takes the form of a bullet 620 that is attached to guide wire 608 near its distal end. The bullet 620 itself is centered about guide wire 608 and is attached thereto by any conventional means such as soldering. Bullet 620 has an interior collection cavity 632 and a leading surface 633 that grows wider proximally without presenting any sharp leading edges. The actual contour may be varied to suit any particular application, with one of the prime concerns being the desired size of the collection cavity 632. The radial size of the proximal end 624 of bullet 620 is slightly less than the radial size of cutter 604.

The cutter 604 is carried by the distal extremity of drive tube 10 and includes annular cutting edge 605 and collection chamber 614. As with any of the described embodiments, the cutter 604 may optionally be provided with a flexible collection chamber as shown in FIGS. 11 and 12.

Figure 20:
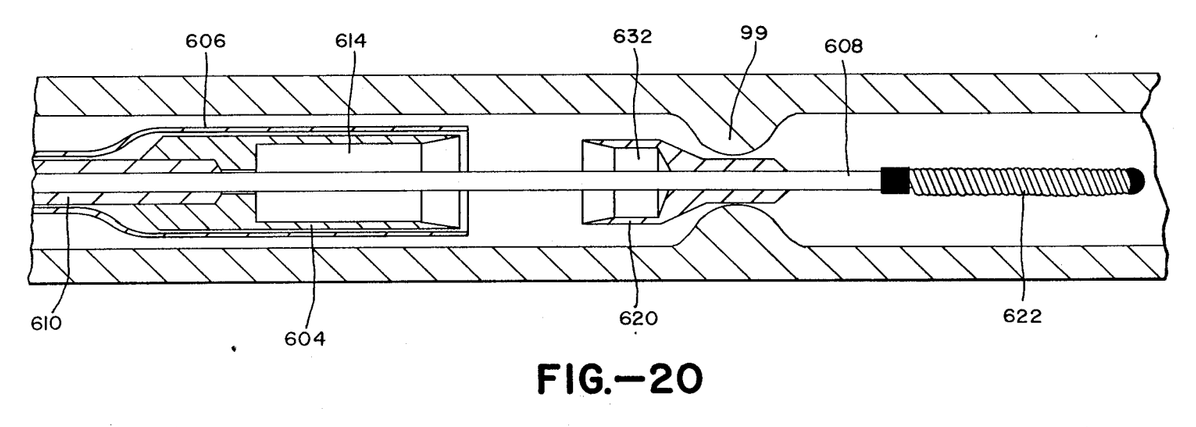
FIG. 20 is a cut-away side elevational view of the cutter assembly shown in FIG. 18 positioned next to an atheroma before a cut is made.
Figure 21:
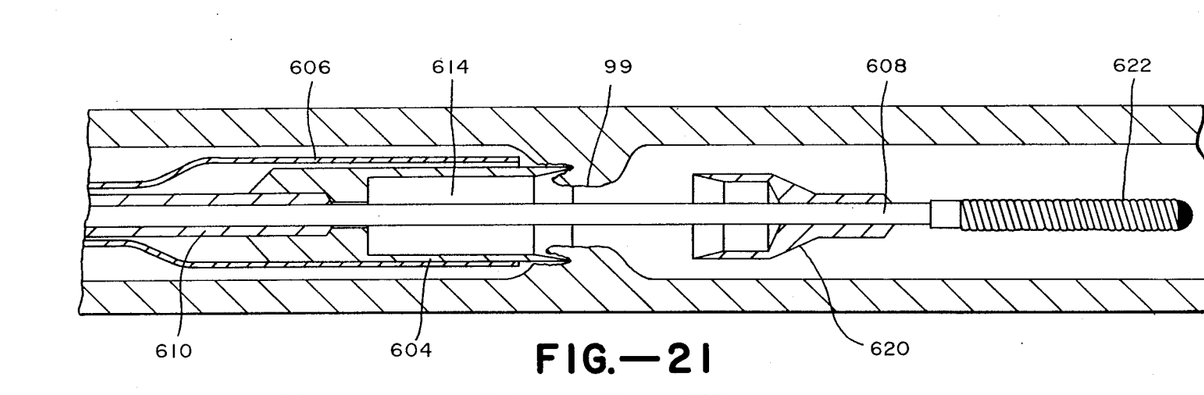
FIG. 21 is a cut-away side elevational view of the cutter assembly embodiment shown in FIGS. 18 and 20 in the process of cutting through an atheroma.
Figure 22:
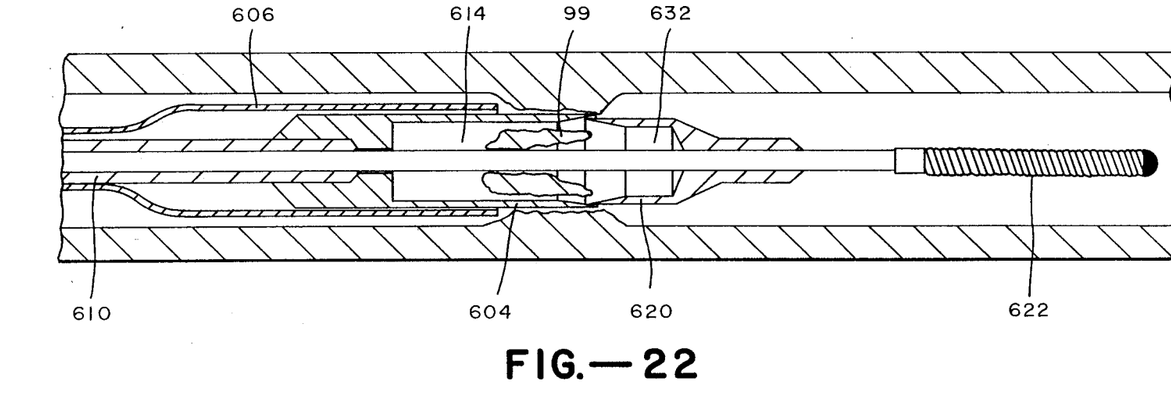
FIG. 22 is a cut-away side elevational view of the cutter embodiment shown in FIGS. 18, 20 and 21 after just completing a pass through the atheroma.

Referring specifically to FIGS. 20–22, the operation of the bullet cutter will be described. A guide wire 608 having an attached bullet 620 is inserted through the occluded artery and positioned such that bullet 620 is locate just before the atheroma. The cutter assembly 602 may then be inserted into the artery over guide wire 608 and advanced until cutting edge 605 is positioned just slightly behind the proximal side of bullet 620. The actual distance between the two components will vary dependent on such factors as the size of both the artery and the atheroma being worked on. By way of example, in the environment of an atherectomy catheter to be used in the main coronary arteries, bullet 620 would be positioned approximately 4 or 5 centimeters from the distal tip of cutter 604. After the cutter is properly positioned, a locking means located on the proximal actuator assembly (not shown) is then actuated to insure that flexible guide wire 608 and drive tube 10 will translate together. Thus, cutter 604 and bullet 620 are then advanced simultaneously through the blockage. Preferably, cutter 604 is rotated at a relatively high rate of speed as it advances, while guide wire 608 and bullet 620 do not rotate at all.

As the cutter assembly advances, the cutter 604 takes a thin shaving from the atheroma since it is slightly wider than the bullet 620. The removed portion of the atheroma is retained within the space between bullet 620 and cutter 604 as well as their respective collection chambers 622 and 614. At the conclusion of the pass, the doctor pulls back on guide wire 608 causing bullet 620 to seat against cutter 604, thereby severing the shaved portion of the atheroma and providing a cap to retain the shavings within the device. The catheter is then removed. It will be apparent that a wire retracting means 645 such as a spring loaded mechanism could be fashioned to selectively automatically seat bullet 620 against cutter 604.

Figure 23:
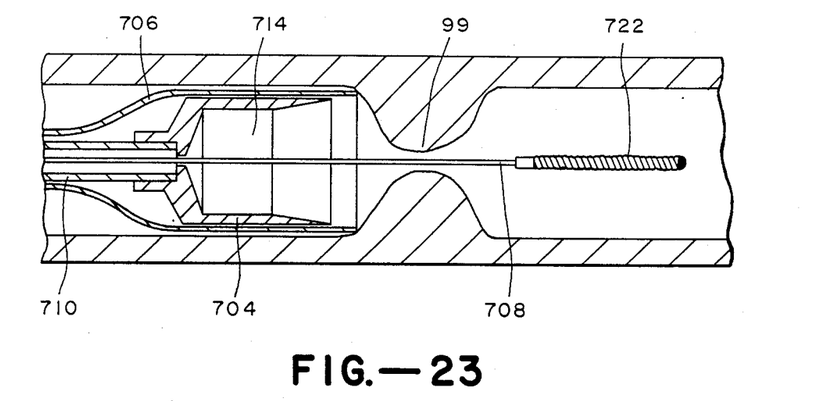
FIG. 23 is a cut-away side elevational view of another embodiment of the cutter assembly of the present invention.
Figure 24:
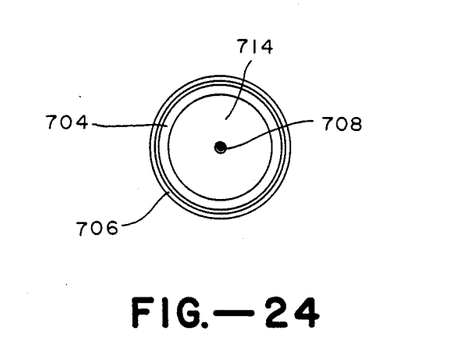
FIG. 24 is a cross-sectional view of the cutter assembly shown in FIG. 23 taken along line 24—24.

Another embodiment of the invention is shown in FIGS. 23-25. The cutter assembly 702 is similar to the previously-described cutter assemblies in that it includes cutter 704 having an annular cutting edge 705 on its distal extremity. A collection chamber 714 is provided within the cutter. In this embodiment, a guide wire 708 having a flexible spring tip 722 is also provided. However, in this embodiment, the device does not include any retaining means carried by the guide wire 708.

The atherectomy devices described herein can have cutters of various sizes. For uses within a blood stream, units having cutter diameters ranging from 12 French down to 3 French are easily provided, thereby making them ideal for surgical treatment of very small diameter vessels. It is apparent from the foregoing that there has been provided an atherectomy device which is particularly efficacious in removing material from atheromas in arterial vessels. The device's particular advantages include that atheromas removed using such surgical removal techniques are less likely to reoccur then atheromas opened using prior vessel clearing techniques.

Although only a few embodiments of the present invention have been described, it should be understood that the present invention may be embodied in many other specific forms without departing from the spirit or scope of the invention. Particularly, it should be noted that the specific proximal actuator assemblies disclosed can be widely varied to effect the drive tube, guide wire and tubular member motions required for particular tasks. Similarly, the features of the various cutting assemblies disclosed may be interchanged to suit a particular application. Therefore, the present examples and embodiments are to be considered as illustrative and not restrictive, and the invention is not to be limited to the details given herein, but may be modified within the scope of the appended claims.

We claim:

1. An atherectomy device for removal of material of an atheroma from a vascular vessel, said device comprising:
   a flexible tubular member adapted to be inserted into the vessel and having proximal and distal extremities,
   flexible drive means having proximal and distal extremities and disposed within said tubular member for rotational and axial movement therein, said drive means extending from the proximal to distal ends of the tubular member,
   a cup-shaped cutter carried by the distal extremity of the flexible drive means, said cutter having a distally extending annular cutting surface and an interior collection chamber, and
   means carried by the proximal extremity of the flexible tubular member and coupled to the flexible drive means for rotating the cutter independently of rotation of the tubular member and for axially extending and retracting the cutter independent of axial movement of the tubular member,
   whereby said cutter is movable axially from a position fully received by the tubular member to an axially extended position wherein the cutting surface is spaced forwardly of the distal extremity of the tubular member so that the cutter is capable of engaging and severing the atheroma with the severed portions of the atheroma being received in the collection chamber.

2. An atherectomy device as in claim 1 wherein said drive means includes a tubular drive cable having a longitudinal passage therethrough.

3. An atherectomy device as in claim 2 wherein said guiding means includes a flexible guide wire mounted for axial movement within the drive cable passage.

4. An atherectomy device as in claim 3 together with retaining means carried by the guide wire for facilitating collection of materials removed from the atheroma by the cutter.

5. An atherectomy device for removal of material of an atheroma from a vessel, said device comprising:
   a flexible tubular member adapted to be inserted into the vessel and having proximal and distal extremities,
   flexible drive means having proximal and distal extremities disposed within said tubular member for rotational and axial movement in the tubular member, said drive means being tubular and having a passage extending longitudinally therethrough,
   a cup-shaped cutter carried by the distal extremity of the flexible drive means, said cutter having a distally extending annular cutting surface and an interior collection chamber,
   means carried by the proximal extremity of the flexible tubular member and coupled to the flexible drive means for rotating the cutting device independent of rotation of the tubular member and for axially extending and retracting the cutter independent of axial movement of the tubular member,
   a flexible guide wire mounted for axial movement in the passage in the drive means, said guide wire extending forward of the cutter, and
   retaining means carried by the guide wire for facilitating collection of materials removed from the atheroma by the cutter.

6. An atherectomy device as in claim 5 wherein said retaining means includes an expandable member together with expansion means for expanding and contracting the expandable member in a radial direction between a first and a second position whereby in the first position the retaining means is collapsed to facilitate insertion of the device into the vessel.

7. An atherectomy device as in claim 6 wherein said expandable member includes a balloon for resisting slippage of the cutter as it cuts through the atheroma.

8. An atherectomy device as in claim 5 wherein the retaining means includes a rigid member having a collection cavity facing the cutter.

9. An atherectomy device as in claim 5 wherein said retaining means allows blood to pass therethrough.

10. An atherectomy device as in claim 6 wherein the expandable member includes an expandable basket having first and second ends.

11. An atherectomy device as in claim 10 wherein the guide wire has a lumen extending therethrough and wherein the expansion means includes an expansion wire disposed within the guide wire lumen and mounted for axial movement relative to the guide wire for expanding and contracting the expandable basket.

12. An atherectomy device as in claim 10 wherein the basket includes a first end secured to the guide wire and a second end mounted for axial translation along the guide wire, the second basket end being adapted to communicate with the flexible drive means for expanding the basket radially.

13. An atherectomy device as in claim 10 wherein the basket is formed of a meshed material.

14. An atherectomy device as in claim 13 wherein the mesh is formed from braided strands.

15. An atherectomy device as in claim 14 wherein the braided strands are stainless steel and the basket is formed from in the range of 16 to 32 strands.

16. An atherectomy device as in claim 1 wherein the collection chamber is flexible.

17. An atherectomy device as in claim 5 wherein the guide wire has a spring tip.

18. An atherectomy device as in claim 1 wherein said tubular member includes a housing for receiving said cutter.

19. An atherectomy device for removal of material of an atheroma from a vessel, said device comprising:
  a flexible tubular member adapted to be inserted into the vessel and having proximal and distal extremities,
  a flexible drive means disposed within the tubular member for rotational and axial movement therein.
  a cup-shaped cutter carried by the flexible drive means, said cutter having a distally extending annular cutting surface and an interior collection chamber,
  a flexible guiding wire extending forward of the cutter for guiding the cutter to travel axially within the vessel, and
  anchoring means carried by the guide wire forward of the cutter for pressing radially to resist slippage by the cutter as it cuts through the atheroma.

20. An atherectomy device as recited in claim 18 wherein said anchoring means includes an inflatable balloon.

21. An atherectomy device as recited in claim 20 wherein said flexible guiding wire has a lumen running axially therethrough to facilitate inflation of the balloon.

22. An atherectomy device as in claim 20 together with an expandable protective sheath that covers all portions of the balloon that contact the cutting edge.

23. An atherectomy device as in claim 22 wherein the protective sheath is formed of braided material.

24. An atherectomy device as recited in claim 19 together with actuator means for moving said cutter into abutting contact with said anchoring means for retaining the removed material within said device.

25. An atherectomy device as in claim 24 wherein said anchoring means includes an expandable member together with means for expanding the expandable member in a radial direction.

26. An atherectomy device as in claim 25 wherein the guiding wire has a lumen running axially therethrough and the expanding means includes an expansion wire disposed within said guiding wire and adapted for axial movement relative to and within the guiding wire for expanding and contracting the expandable member.

27. An atherectomy device as in claim 25 wherein the expandable member is formed of a braided material.

28. An atherectomy device as in claim 27 wherein the braided basket is formed form in the range of 10 and 50 wires.

29. An atherectomy device as in claim 27 wherein the braided basket is formed from in the range of 16 to 32 stainless steel wire.

30. An atherectomy device for removing material of an atheroma from a vessel, said device comprising:
  a flexible tubular member adapted to be inserted into the vessel and having proximal and distal extremities,
  a flexible drive means having proximal and distal extremities and disposed within said tubular member for rotational movement within the tubular member,
  a tubular collection chamber secured to the distal extremity of the flexible drive means, said chamber having an open distal end and a substantially closed proximal end,
  an annular cutting ring secured to the tubular collection chamber, whereby material severed by the ring can enter the collection chamber,
  a sheath for receiving said cutting means such that at least a portion of the cutting edge is not exposed,
  actuator means carried by the proximal extremity of the flexible tubular member and coupled to the flexible drive means for rotating the cutting device independent of rotation of the tubular member,
  translating means for simultaneously moving said cutting means and said sheath relative to said tubular member,
  flexible guiding means extending forward of the cutter for guiding the cutter to travel axially within the vessel, and
  retention means carried by the guiding means forwardly of the cutting means for cooperating with the collection means to collect removed atheroma material within the atherectomy device.

31. An atherectomy device as in claim 30 wherein the cutting means further includes a collection chamber for retaining the removed atheroma material.

32. An atherectomy device as in claim 31 wherein the retention means includes a basket expandable in a radial direction, the basket formed to act as a cover for the collection chamber for retaining the severed atheroma materials.

33. An atheroma device for removal of material of an atheroma from a vessel, said device comprising:
  a flexible tubular member adapted to be inserted into the vessel,
  a flexible drive means disposed within the tubular member for rotational and axial movement therein, a cup-shaped cutter carried by the flexible drive means, said cutter having a forwardly extending annular cutting surface and an interior collection chamber, a flexible guiding wire extending forward of the cutter for guiding the cutter to travel axially within the vessel, retention means carried by the guide wire forward of the cutter for collecting the removed atheroma material within the atherectomy device, said retention means including an expandable member.

34. An atherectomy device as in claim 33 wherein the collection chamber is flexible.

35. An atheroma device for removal of material of an atheroma from a vessel, said device comprising:
a flexible tubular member,
a tubular flexible drive means disposed within said tubular member for rotational movement in the tubular member,
a cup-shaped cutter carried by the distal extremity of the flexible drive means, the cutter having a forwardly extending annular cutting surface and an interior collection chamber,
a flexible guide wire disposed within the drive means and mounted for axial movement therein, said guide wire extending beyond the distal extremity of the cutter, and being rotationally decoupled therefrom,
a retention means carried by the guide wire distally to the cutter for facilitating collection of materials removed from the atheroma by the cutter, and
means for translating the cutter and the retention means relative to each other.

36. An atherectomy device as in claim 35 wherein the retention means includes a rigid member having a smaller diameter than the cutter.

37. An atherectomy device as in claim 36 wherein the rigid member has a collection cavity extending from its proximal extremity for retaining materials removed from the atheroma by the cutter.

38. An atherectomy device as in claim 35 wherein the cutting surface is a rigid ring and the collection chamber is flexible and secured proximally of the ring.

39. A method for removing at least a portion of an atheroma from a blood vessel, the method comprising the steps of:
advancing a guide wire into the vessel to a position so that at least a portion of an expandable member carried by the guide wire is positioned distally to the portion of the atheroma to be removed;
advancing a cutter over the guide wire through the atheroma towards the expandable member for removing a portion of the atheroma;
expanding the expandable member within the vessel in the radial direction; and
bringing the cutter into contact with the expanded expandable, whereby the atheroma is severed.

40. A method as in claim 39 wherein the steps are repeated to remove additional portions of the atheroma until sufficient portions of the atheroma are removed to provide a relatively good flow passage in the vessel through the atheroma.

41. A method as in claim 39 wherein the cutter is rotated relative to the atheroma while the cutter is being advanced.

42. A method as in claim 41 together with the step of egressing the cutter from the housing while it is being advanced.

43. A method as in claim 41 wherein the expanding step occurs before the cutting step and the expandable member is adapted to resist slippage of the cutter as it cuts through the atheroma.

44. A method for removing at least a portion of an atheroma from a blood vessel, the method comprising the steps of:
advancing a guide wire into the vessel to a position in the vicinity of the atheroma to be removed;
advancing a cup-shaped cutter over the guide wire into the vessel to a position proximal to the portion of the atheroma to be removed, said cutter having an annular cutting surface and an interior collection chamber; and
simultaneously rotating and advancing the cutter, the advancement causing the cutter to egress from the housing, whereby the atheroma is severed and the severed portions of atheroma are collected in the collection chamber.

45. A method as in claim 44 wherein the guide wire carries a retention means distally to the cutter, together with the step of drawing the retention means into abutment with the cutter to entrap the severed portions of atheroma therein.

46. A method as in claim 45 together with the step of expanding the retention means.

47. In a method for removing at least a portion of an atheroma from a vessel using an atherectomy device having a flexible tubular member, a cutter carried by the distal extremity of a flexible tubular drive means disposed within the tubular member and mounted for rotational movement therein, a flexible guide wire passing axially through the tubular drive means and adapted for axial movement therein, the guide wire carrying a retention means near its distal extremity, the method comprising the steps of:
inserting the guide wire and retention means into the vessel;
advancing the retention means within the vessel to a desired position proximal to the atheroma materials to be removed;
guiding the cutter to a position within the vessel that is a selected distance proximal to the retention means;
rotating the cutter while simultaneously advancing the retention means and the cutter through the atheroma for removing a portion of the atheroma while maintaining the fixed spacing;
collecting the removed portions of atheroma;
drawing the retaining means into abutment with the cutter for retention of the collected atheroma materials within the atherectomy device; and
withdrawing the cutter and retention means carrying the collected portions of atheroma from the vessel.

48. In a method for removing at least a portion of an atheroma from a vessel using an atherectomy device having a flexible tubular member, a cutter carried by the distal extremity of a flexible tubular drive means disposed within the tubular member and mounted for rotational movement therein, a flexible guide wire passing axially through the tubular drive means and adapted for axial movement therein, the guide wire carrying an expandable member near its distal extremity, the method comprising the steps of:

inserting the guide wire and expandable member into the vessel;

advancing the expandable member within the vessel to a first desired position relative to the atheroma materials to be removed;

guiding the cutter to a second desired position within the vessel that is proximal to the atheroma materials to be removed;

expanding the expandable member to anchor the atherectomy device at a position distal to the cutting assembly;

simultaneously rotating and advancing the cutter to remove a portion of the atheroma;

collecting the removed portions of atheroma;

drawing the expandable member into abutment with the cutter for retaining the collected atheroma materials within the atherectomy device; and withdrawing the collected portions of atheroma from the vessel.

49. An atherectomy device as in claim 8, wherein the rigid member is cylindrical, tapered on the distal end facing away from the cutter, and includes a circular blade on the proximal end facing the cutter.

50. An atherectomy device as in claim 49, wherein, the cylindrical diameter is slightly less than that of the cutter.

51. An atherectomy device as in claim 50, wherein the cutter includes an interior collection chamber at its distal end facing the rigid member, whereby the rigid member can be drawn into said chamber to effect cutoff of severed atheroma.

* * * * *